United States Patent
Shuber et al.

(10) Patent No.: US 10,527,608 B2
(45) Date of Patent: Jan. 7, 2020

(54) METHODS FOR RARE EVENT DETECTION

(71) Applicant: GENETICS RESEARCH, LLC, Wakefield, MA (US)

(72) Inventors: Anthony P. Shuber, Wakefield, MA (US); William Glover, Wakefield, MA (US)

(73) Assignee: GENETICS RESEARCH, LLC, Waltham, MA (US)

( * ) Notice: Subject to any disclaimer, the term of this patent is extended or adjusted under 35 U.S.C. 154(b) by 0 days.

(21) Appl. No.: 15/877,619

(22) Filed: Jan. 23, 2018

(65) Prior Publication Data
US 2018/0356410 A1 Dec. 13, 2018

Related U.S. Application Data

(60) Provisional application No. 62/568,121, filed on Oct. 4, 2017, provisional application No. 62/526,091, filed on Jun. 28, 2017, provisional application No. 62/519,051, filed on Jun. 13, 2017.

(51) Int. Cl.
| | |
|---|---|
| *G01N 33/53* | (2006.01) |
| *G01N 33/487* | (2006.01) |
| *C12Q 1/68* | (2018.01) |
| *C12N 9/22* | (2006.01) |
| *G01N 33/50* | (2006.01) |
| *G01N 33/574* | (2006.01) |
| *C12Q 1/683* | (2018.01) |
| *C12Q 1/6886* | (2018.01) |
| *C12Q 1/6897* | (2018.01) |
| *G01N 33/533* | (2006.01) |

(52) U.S. Cl.
CPC ........... *G01N 33/5308* (2013.01); *C12N 9/22* (2013.01); *C12Q 1/683* (2013.01); *C12Q 1/6886* (2013.01); *C12Q 1/6897* (2013.01); *G01N 33/487* (2013.01); *G01N 33/5091* (2013.01); *G01N 33/533* (2013.01); *G01N 33/574* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 6,297,010 B1 | 10/2001 | Stefano | |
| 8,318,445 B2 | 11/2012 | Bernard et al. | |
| 8,916,530 B2 | 12/2014 | Shanahan et al. | |
| 10,011,849 B1 | 7/2018 | Gill et al. | |
| 10,081,829 B1 | 9/2018 | Shuber et al. | |
| 2003/0215854 A1 | 11/2003 | Clausen et al. | |
| 2004/0197804 A1 | 10/2004 | Keefe et al. | |
| 2006/0183109 A1 | 8/2006 | Dahlberg et al. | |
| 2008/0254516 A1 | 10/2008 | St. John et al. | |
| 2009/0053715 A1 | 2/2009 | Dahlhauser | |
| 2009/0325169 A1 | 12/2009 | Walder et al. | |
| 2012/0315633 A1 | 12/2012 | Mantzaris et al. | |
| 2013/0059762 A1 | 3/2013 | Leamon et al. | |
| 2014/0356867 A1 | 12/2014 | Peter et al. | |
| 2015/0105284 A1 | 4/2015 | Willson et al. | |
| 2015/0211058 A1 | 7/2015 | Carstens | |
| 2015/0292033 A1 | 10/2015 | Wang et al. | |
| 2015/0329917 A1 | 11/2015 | Shuber | |
| 2016/0002720 A1 | 1/2016 | Richard | |
| 2016/0017396 A1 | 1/2016 | Cann et al. | |
| 2016/0130664 A1 | 5/2016 | Albitar | |
| 2016/0153005 A1 | 6/2016 | Zhang et al. | |
| 2016/0319262 A1* | 11/2016 | Doudna | C12N 9/22 |
| 2017/0014449 A1 | 1/2017 | Bangera et al. | |
| 2017/0022551 A1 | 1/2017 | Liu et al. | |
| 2017/0044592 A1 | 2/2017 | Peter et al. | |
| 2017/0053062 A1 | 2/2017 | Cradick et al. | |
| 2017/0114413 A1 | 4/2017 | Hahn et al. | |

FOREIGN PATENT DOCUMENTS

| | | |
|---|---|---|
| EP | 3150718 A1 | 4/2017 |
| WO | 1995/006752 A1 | 3/1995 |
| WO | 99/39003 A1 | 8/1999 |
| WO | 2000/011222 A1 | 3/2000 |
| WO | 2003/027258 A2 | 4/2003 |

(Continued)

OTHER PUBLICATIONS

Hahn, 2009, Microsystem for isolation of fetal DNA from maternal plasma by preparative size separation, Clin Chem 55 (12):2144-2152.

Zischewski, 2017, Detection of on-target and off-target mutations generated by CRISPR/Cas9 and other sequence-specific nucleases, Biotech Adv 35(1):95-104.

Larsson, 2004, In situ genotyping individual DNA molecules by target-primed rolling-circle amplification of padlock probes, Nat Meth 1(3):227-232.

Hsieh, 2010, Electrochemical DNA detection via exonuclease and target-catalyzed transformation of surface-bound probes, Langmuir 26(12):10392-10396.

Campesato, 2015, Comprehensive cancer-gene panels can be used to estimate mutational load and predict clinical benefit to PD-1 blockade in clinical practice, Oncotarget 6(33):34221-34227.

(Continued)

Primary Examiner — Nancy A Treptow
(74) Attorney, Agent, or Firm — Brown Rudnick LLP; Thomas C. Meyers

(57) ABSTRACT

The invention provides methods for detecting small mutations and structural alterations in DNA by using binding proteins to protect those features while digesting unprotected DNA in a sample. To detect small mutations, a protein that binds exclusively to the mutation of interest, and not to wild-type, is used. For structural alterations, binding proteins are used that flank a breakpoint of the alteration. After digestion of unbound, unprotected nucleic acid in the sample, the mutation- or breakpoint-containing segment remains as an isolated DNA fragment. The sample is then assayed to detect any fragment of DNA and the detection of the fragment indicates the presence of the mutation or breakpoint in the subject.

23 Claims, 9 Drawing Sheets

(56) References Cited

FOREIGN PATENT DOCUMENTS

| | | |
|---|---|---|
| WO | 2008/104794 A2 | 9/2008 |
| WO | 2010/014920 A1 | 2/2010 |
| WO | 2015/075056 A1 | 5/2015 |
| WO | 2016/014409 A1 | 1/2016 |
| WO | 2016/028843 A2 | 2/2016 |
| WO | 2016/028887 A1 | 2/2016 |
| WO | 2016/094867 A1 | 6/2016 |
| WO | 2016/100955 A2 | 6/2016 |
| WO | 2016/100974 A1 | 6/2016 |
| WO | 2016/134136 A2 | 8/2016 |
| WO | 2016/144810 A1 | 9/2016 |
| WO | 2016/172727 A1 | 10/2016 |
| WO | 2016/186946 A1 | 11/2016 |
| WO | 2017/031360 A1 | 2/2017 |
| WO | 2017/053762 A1 | 3/2017 |
| WO | 2017/218512 A1 | 12/2017 |
| WO | 2018/068028 A1 | 4/2018 |

OTHER PUBLICATIONS

Chalmers, 2017, Analysis of 100,000 human cancer genomes reveals the landscape of tumor mutational burden, Genome Med 9(34):1-14.
Schaefer, 2017, Unexpected mutations after CRISPR-Cas9 editing in vivo, Nat Meth 14(6):547-550.
Lescarbeau, 2017, A reanalysis of Schaefer et al does not indicate extensive CRISPR/Cas9 mediated off-target editing events, bioRxiv.
Zehir, 2017, Mutational landscape of metastatic cancer revealed from prospective clinical sequencing of 10,000 patients, Nat Med 23(6):703-713.
Tosi, 2017, Long-adapter single-strand oligonucleotide probes for the massively multiplexed cloning of kilobase genome regions, Nat Biomed Eng 1:92.
Pattanayak, 2013, High-throughput profiling of off-target DNA cleavage reveals RNA-programmed Cas9 nuclease specificity, Nat Biotech 31(9)839-843.
Fu, 2013, High frequency off-target mutagenesis induced by CRISPR-Cas nucleases in human cells, Nat Biotech 31(9) 822-826.
Hsu, 2013, DNA targeting specificity of RNA-guided Cas9 nucleases, Nat Biotech 31(9):827-832.
Zhang, 2015, Use of genome-wide association studies for cancer research and drug repositioning, PLoS One 10(3): e0116477.
Wang, 2014, Genetic screens in human cells using the CRISPR/Cas9 system, Science 343(6166):80-84.
Leung, 2012, Luminescent detection of DNA-binding proteins, Nucleic Acids Res 40(3):941-55.
Xu, 2015, An improved protocol for small RNA library construction using high definition adapters, Meth Next-Gen Seq 2:1-10.
Zhang, 2018, Detection of target DNA with a novel Cas9/sgRNAs-associated reverse PCR (CARP) technique, Anal Bioanal Chem 410(12):2889-2900.
International Search Report and written Opinion dated Aug. 27, 2018, for PCT/US2018/037294, filed Jun. 13, 2018 (10 pages).
International Search Report and written Opinion dated Aug. 28, 2018, for PCT/US2018/037273, filed Jun. 13, 2018 (10 pages).
International Search Report and written Opinion dated Sep. 13, 2018, for PCT/US2018/037296, filed Jun. 13, 2018 (11 pages).
International Search Report and written Opinion dated Sep. 17, 2018, for PCT/US2018/037277, filed Jun. 13, 2018 (9 pages).
International Search Report and written Opinion dated Sep. 26, 2018, for PCT/US2018/037280, filed Jun. 13, 2018 (18 pages).
International Search Report and written Opinion dated Aug. 27, 2018, for PCT/US2018/037312, filed Jun. 13, 2018 (10 pages).
International Search Report and written Opinion dated Sep. 12, 2018, for PCT/US2018/037307, filed Jun. 13, 2018 (8 pages).
International Search Report and written Opinion dated Sep. 11, 2018, for PCT/US2018/037310, filed Jun. 13, 2018 (8 pages).
International Search Report and written Opinion dated Aug. 29, 2018, for PCT/US2018/037287, filed Jun. 13, 2018 (10 pages).
International Search Report and written Opinion dated Sep. 21, 2018, for PCT/US2018/039518, filed Jun. 26, 2018 (8 pages).
Chen, 2018, CRISPR-Cas12a target binding unleashes indiscriminate single-stranded DNase activity, Science aar6245 (8 pages).
Gootenberg, 2018, Multiplexed and portable nucleic acid detection platform with Cas13, Cas12a, and Csm6, Science aaq0179 (10 pages).
Lee, 2017, CUT-PCR: CRISPR-mediated ultrasensitive detection of target DNA using PCR, Ocogene 36 (49):6823-6829.
Wang, 2018, CRISPR-typing PCR (ctPCR), a new Cas9-based DNA detection method, Sci Rep 8(1):14126.
International Search Report and Written Opinion dated Aug. 29, 2018, for PCT/US18/37287, filed Jun. 13, 2018 (10 pages).
International Search Report and Written Opinion dated Dec. 20, 2018, for PCT/US18/54188, filed Oct. 3, 2018 (8 pages).
International Search Report and Written Opinion dated Jan. 15, 2019, for PCT/US18/55648, filed Oct. 12, 2018 (7 pages).
International Search Report and Written Opinion dated Nov. 7, 2018, for PCT/US18/37337, filed Jun. 13, 2018 (12 pages).
International Search Report and Written Opinion dated Sep. 21, 2018, for PCT/US18/39518, filed Jun. 26, 2018 (7 pages).
Kurdykov, 2016, DNA Methylation analysis: choosing the right method, Biology 5(1):1-21.
Stunkel, 2001, Programming the transcriptional state of replicating methylated DNA, J Biol Chem 276(23):20743-20749.
Altmuller, 2014, Enrichment of target sequence for next-generation sequencing applications in research and diagnostics, Biol Chem 395(2):231-37.
Deleavey, 2012, Designing chemically modified oligonucleotides for targeted gene silencing, Chem Biol 19(8):937-54.
Harrington, 2017, A thermostable Cas9 with increased lifetime in human plasma, Nat Commun 8(1):1424.
Jiang, 2015, Cas9-assisted targeting of chromosome segments catch enables one-step targeted cloning of large gene clusters.
Jinek, 2012, A programmable dual-RNA-guided DNA endonuclease in adaptive bacterial immunity, Science 337(6096):816-821.
Kozarewa, 2015, Overview of Target Enrichment Strategies, Curr Protoc Mol Biol 112(7):1-23.
Mertes, 2011, Targeted enrichment of genomic DNA regions for next-generation sequencing, Brief Funct Genomics 10(6):374-86.
Monia, 1996, Nuclease resistance and antisense activity of modified oligonucleotides targeted to Ha-ras, J Biol Chem 271(24):14533-40.
Zetsche, 2015, Cpf1 is a single RNA-guided endonuclease of a class 2 CRISPR-Cas system, Cell 163(2):759-71.
Zischewski, 2017, Detection of on-target and off-target mutations generated by CRISPR/Cas9 and other sequence-specific nucleases, Biotechnology Advances 65:95-104.

\* cited by examiner

METHODS FOR RARE EVENT DETECTION

CROSS-REFERENCE TO RELATED APPLICATIONS

This application claims the benefit of, and priority to, U.S. Provisional Application No. 62/568,121, filed Oct. 4, 2017, U.S. Provisional Application No. 62/526,091, filed Jun. 28, 2017, and U.S. Provisional Application No. 62/519,051, filed Jun. 13, 2017, the contents of each of which are incorporated by reference.

TECHNICAL FIELD

The disclosure relates to molecular genetics.

BACKGROUND

DNA has the potential to provide clinically actionable information about a subject. For example, DNA from a tumor can reveal whether a cancer patient is in remission, or may inform a physician about immunotherapy treatments that may be effective for the patient. Similarly, fetal DNA can be studied to detect inherited genetic disorders, aneuploidy, or preeclampsia. However, a consistent challenge in accessing the actionable genetic information lies in existing approaches to sequencing DNA.

Typical DNA sequencing assays include the use of next-generation sequencing (NGS) platforms to capture, amplify, and sequence a subject's DNA. However, typical NGS platforms face a number of challenges. Detecting rare mutations such as a mutation in circulating tumor DNA in a plasma sample that also contains an abundance of "normal", somatic DNA, requires successfully amplifying that tumor DNA for sequencing. Detecting structural alterations such as translocations, inversions, copy number variations, loss of heterozygosity, or large insertions or deletions (indels) is particularly difficult since NGS platforms give a large number of short reads for which assembly is made difficult by such structural alterations.

SUMMARY

The invention provides methods for detecting small mutations and structural alterations in DNA by using binding proteins to protect those features while digesting unprotected DNA in a sample. To detect small mutations, a protein that binds exclusively to the mutation of interest, and not to wild-type, is used. For structural alterations, binding proteins are used that flank a breakpoint of the alteration. After digestion of unbound, unprotected nucleic acid in the sample, the mutation- or breakpoint-containing segment remains as an isolated DNA fragment. The sample is then assayed to detect the fragment and the detection of the fragment indicates the presence of the mutation or breakpoint in the subject.

Embodiments of the invention use proteins that are originally encoded by genes that are associated with clustered regularly interspaced short palindromic repeats (CRISPR) in bacterial genomes. Preferred embodiments use a CRISPR-associated (Cas) endonuclease. For such embodiments, the binding protein in a Cas endonuclease complexed with a guide RNA that targets the Cas endonuclease to a specific sequence. The complexes bind to the specific sequences in the nucleic acid segment by virtue of the targeting portion of the guide RNAs. When the Cas endonuclease/guide RNA complex binds to a nucleic acid segment, the complex protects that segment from digestion by exonuclease. When two Cas endonuclease/guide RNA complexes bind to a segment, they protect both ends of the segment, and exonuclease can be used to promiscuously digest un-protected nucleic acid leaving behind an isolated fragment—the segment of DNA between two bound complexes.

Structural alterations are detected using guide RNAs designed to hybridize to targets flanking a boundary of the alteration. Using two such guide RNAs, first and second Cas endonucleases will bind to the nucleic acid in positions that flank the breakpoint, thereby defining and protecting the segment of nucleic acid that includes the breakpoint. In the absence of the alteration, the two Cas endonuclease/guide RNA complexes will not bind to the same strand, and all of the nucleic acid will end up digested upon exposure to exonuclease. Small mutations, such as substitutions or small indels, are detected using an allele-specific guide RNA—a guide RNA that binds the Cas endonuclease exclusively to the mutation of interest. An allele-specific guide RNA may be used in conjunction with another guide RNA that binds a Cas endonuclease to the same nuclei acid, so that the two Cas endonuclease/guide RNA complexes define and protect a segment between them, but only do so when the small mutation is present in the sample. Accordingly, the invention provides methods for selectively isolating segments of nucleic acid that contain clinically relevant mutations.

Protecting a segment of target nucleic acid with two binding proteins while promiscuously digesting unprotected nucleic acid may be described as a negative enrichment for the target. Embodiments of negative enrichment may be used for the detection of "rare events" where a specific sequence of interest makes up a very small percentage of the total quantity of starting material. Specifically, negative enrichment techniques may be used to detect specific mutations in circulating tumor DNA (ctDNA) in the plasma of cancer patients, or specific mutations of interest potentially associated with fetal DNA circulating in maternal plasma. In addition negative enrichment analysis can be applied to purified circulating tumor cells (CTCs).

In one embodiment a single or a cocktail of Cas9/gRNA complex(es) are created with the gRNA(s) designed specifically to target a region in the genome known to be associated with a clinically relevant fusion event. The sample of interest is exposed to both Cas9/gRNA complexes or cocktail of complexes and subsequently analyzed by a negative enrichment assay.

Thus the invention provides methods for the detection of clinically actionable information about a subject. Methods of the invention may be used to with tumor DNA to monitor cancer remission, or to inform immunotherapy treatment. Methods may be used with fetal DNA to detect, for example, mutations characteristic of inherited genetic disorders. Methods may be used to detect and describe mutations and/or alterations in circulating tumor DNA in a blood or plasma sample that also contains an abundance of "normal", somatic DNA, Methods may be used for directly detecting structural alterations such as translocations, inversions, copy number variations, loss of heterozygosity, or large indels. The subject DNA may include circulating tumor DNA in a patient's blood or plasma, or fetal DNA in maternal blood or plasma.

In certain aspects, the invention provides a method for detecting a structural genomic alteration. The method includes protecting a segment of nucleic acid in a sample by introducing Cas endonuclease/guide RNA complexes that bind to targets that flank a boundary of a genomic alteration, digesting unprotected nucleic acid, and detecting the segment, thereby confirming the presence of the genomic alteration. The digesting step may include exposing the unprotected nucleic acid to one or more exonucleases. Preferably, the Cas endonuclease/guide RNA complexes include guide RNAs with targeting regions complementary to targets that do not appear on the same chromosome in a healthy human genome.

After digestion, the protected segment of nucleic acid may be detected or analyzed by any suitable method. For example, the segment may be detected or analyzed by DNA staining, spectrophotometry, sequencing, fluorescent probe hybridization, fluorescence resonance energy transfer, optical microscopy, electron microscopy, others, or combinations thereof. The segment may be of any suitable length. Methods of the invention are useful for isolation of long fragments of DNA, and the digesting step may include isolating the segment as an intact fragment of DNA with a length of at least five thousand bases. Short fragments may be isolated in some embodiments, e.g., fragments with about 50 to a few hundred bases in length.

The method may include providing a report describing the presence of the genomic alteration in a genome of a subject.

In some embodiments, the sample includes plasma from the subject and the segment is cell-free DNA (cfDNA). The plasma may be maternal plasma and the segment may be of fetal DNA. In certain embodiments, the sample includes plasma from the subject and the segment is circulating tumor DNA (ctDNA). In some embodiments, the sample includes at least one circulating tumor cell from a tumor and the segment is tumor DNA from the tumor cell.

Aspects of the invention provide a method for detecting a mutation. The method includes protecting a segment of a nucleic acid in a sample by introducing first Cas endonuclease/guide RNA complex that binds to a mutation in the nucleic acid and a second such complex that also binds to the same nucleic acid. The first and second Cas endonuclease/guide RNA complexes bind to the nucleic acid to define and protect a segment of the nucleic acid, and—by virtue of the mutation-specific binding of at least the first complex—only bind to, and protect, the segment in the presence of the mutation. The method includes digesting unprotected nucleic acid and detecting the segment, there confirming the presence of the mutation. The digesting step may include exposing the unprotected nucleic acid to one or more exonucleases.

In preferred embodiments, the first Cas endonuclease/guide RNA complex includes a guide RNA with targeting region that binds to the mutation but that does not bind to other variants at a loci of the mutation. The detecting step may include DNA staining, spectrophotometry, sequencing, fluorescent probe hybridization, fluorescence resonance energy transfer, optical microscopy, electron microscopy, others, or combinations thereof. The digesting step may include isolating the segment as an intact fragment of DNA, which fragment may have any suitable length (e.g., about ten to a few hundred bases, a few hundred to a few thousand bases, at least about five thousand bases, etc.). The method may include providing a report describing the presence of the mutation in a genome of a subject.

In some embodiments, the sample includes plasma from the subject and the segment is cell-free DNA (cfDNA). For example, the plasma may be maternal plasma and the segment may be of fetal DNA. In certain embodiments, the sample includes plasma from the subject and the segment is circulating tumor DNA (ctDNA). Optionally, the sample includes at least one circulating tumor cell from a tumor and the segment comprises tumor DNA from the tumor cell.

DETAILED DESCRIPTION

Figure 1:
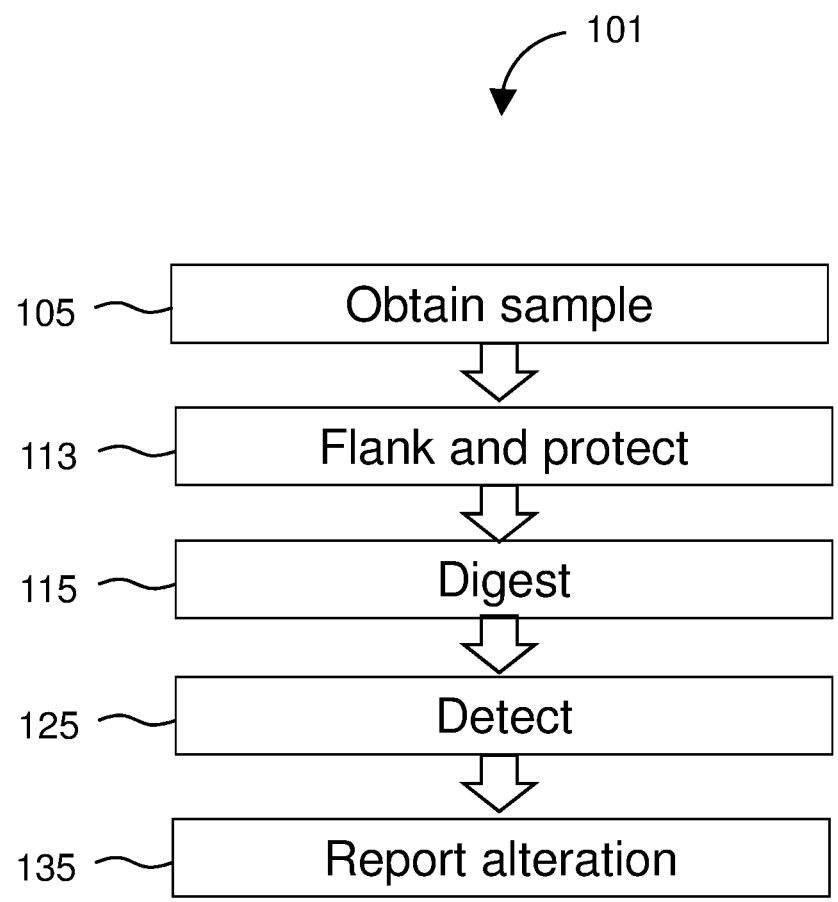
FIG. 1 diagrams a method for detecting a structural genomic alteration.

FIG. 1 diagrams a method 101 for detecting a structural genomic alteration. The method 101 includes obtaining a sample that includes DNA from a subject. Binding proteins are introduced to protect 113 a segment of nucleic acid in the sample. The binding proteins bind to specific targets that flank a boundary of a genomic alteration. The method 101 includes digesting 115 unprotected nucleic acid and detecting 125 the segment, there confirming the presence of the genomic alteration in the subject. A report 135 may be provided that describes the alteration as being present in the subject.

Any suitable structural genomic alteration may be detected using the method 101. Suitable structural alterations may include, for example, inversions, translocations, copy number variations, or gene duplications. Binding proteins are used that will flank a boundary of the structural alteration only when the alteration is present. For example, binding proteins may be used that—in the absence of the alteration—bind to different chromosomes of a human genome. Methods of the invention are used to detect the alteration in a DNA sample from a subject.

Figure 2:
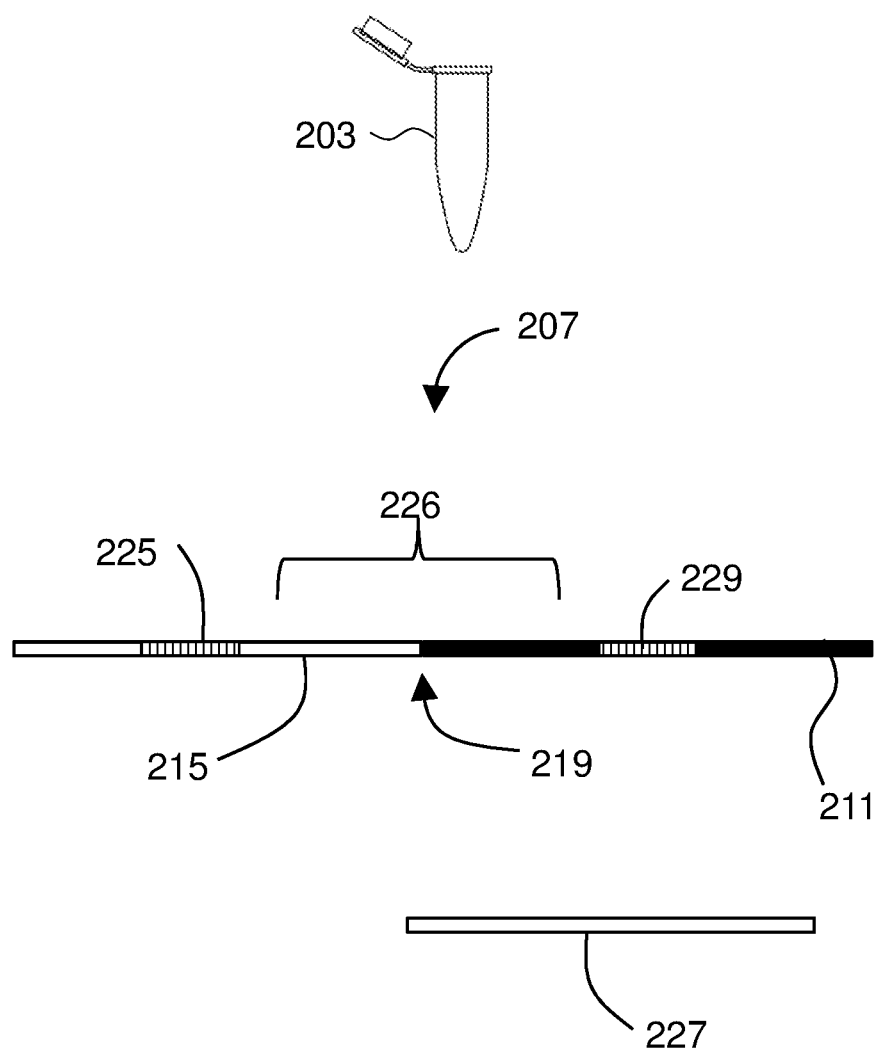
FIG. 2 illustrates a sample that includes DNA from a subject.

FIG. 2 illustrates a sample 203 that includes DNA 207 from a subject. The DNA 207 may be any suitable DNA and in preferred embodiments includes cell-free DNA, such as circulating tumor DNA (ctDNA) or fetal DNA from maternal blood or plasma. The sample may include plasma from the subject in which the segment is cell-free DNA (cfDNA). In some embodiments, the sample 203 includes maternal plasma and fetal DNA. In certain embodiments, ctDNA is in the sample 203. In some embodiments, the sample 203 includes at least one circulating tumor cell from a tumor and the segment comprises tumor DNA from the tumor cell.

Methods may include detection or isolation of circulating tumour cells (CTCs) from a blood sample. Cytometric approaches use immunostaining profiles to identify CTCs. CTC methods may employ an enrichment step to optimize the probability of rare cell detection, achievable through immune-magnetic separation, centrifugation or filtration. Cytometric CTC technology includes the CTC analysis platform sold under the trademark CELLSEARCH by Veridex LLC (Huntingdon Valley, Pa.). Such systems provide semi-automation and proven reproducibility, reliability, sensitivity, linearity and accuracy. See Krebs, 2010, Circulating tumor cells, Ther Adv Med Oncol 2(6):351-365 and Miller, 2010, Significance of circulating tumor cells detected by the CellSearch system in patients with metastatic breast colorectal and prostate cancer, J Oncol 2010:617421-617421, both incorporated by reference.

In the illustrated example, the DNA 207 has a portion 211 that originated from a first chromosome and a second portion 215 that originated from a different chromosome. By virtue of a translocation between the two chromosomes, the DNA 207 includes a breakpoint 219 of the translocation. The DNA also includes a first binding target 229 for a first binding protein and a second binding target 225 for second binding protein. The two binding targets 229, 225 flank the breakpoint 219, which lies in a segment 226 between the two binding targets. The sample may include other nucleic acid 227 that does not include the targets or the breakpoint. The method includes binding the binding proteins to the targets 225, 229.

Figure 3:
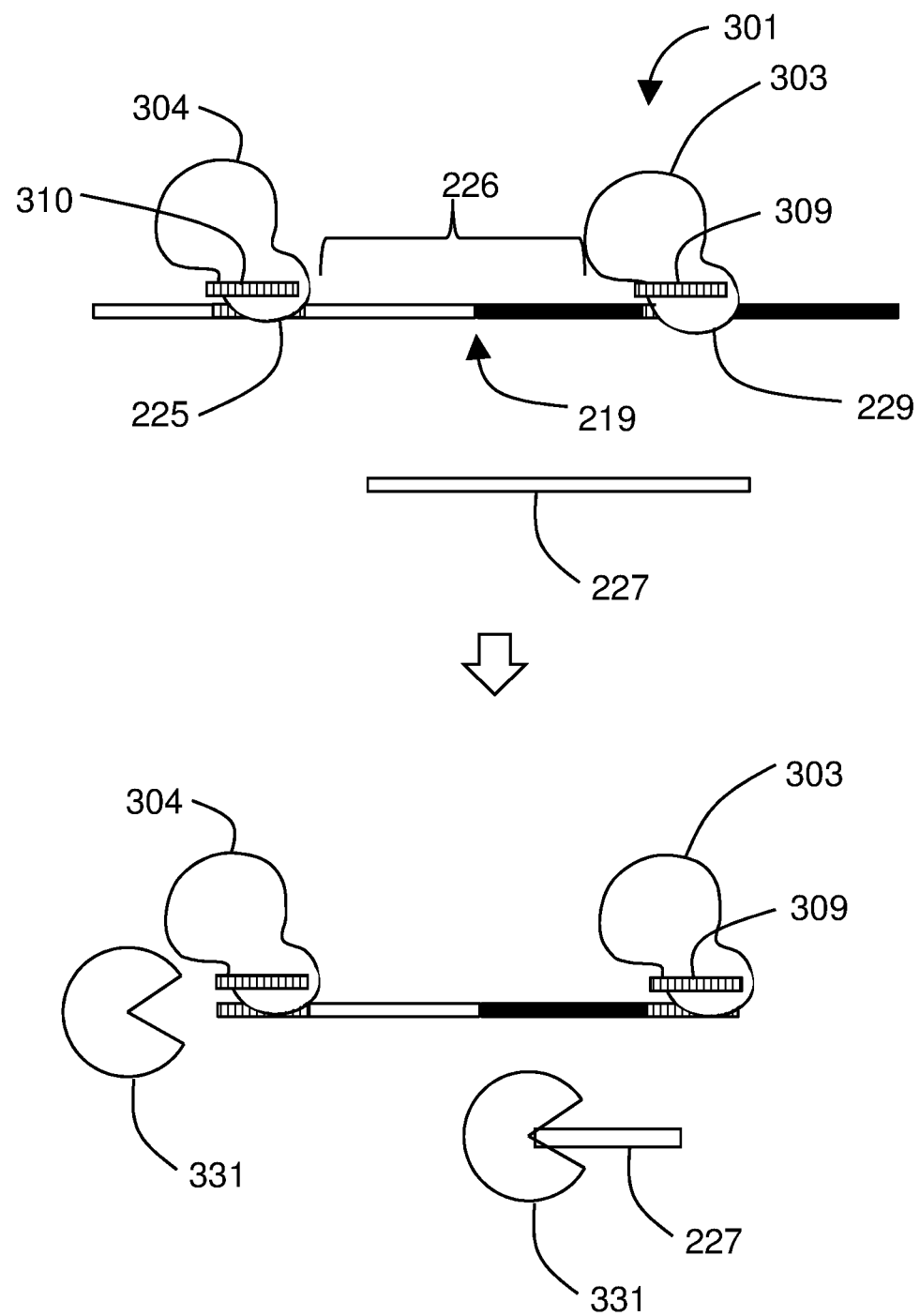
FIG. 3 shows binding proteins protecting a DNA segment that includes a breakpoint.

FIG. 3 shows binding proteins 301 being introduced to protect 113 the segment 226 of nucleic acid where the breakpoint 219 lies. The binding proteins 301 bind to specific targets that flank a boundary of a genomic alteration. The depicted method for isolating the segment 226 may be described as a negative enrichment. Contrary to the standard approach of enriching a specific genomic sequence of interest away from a heterogeneous background of DNA by trying to fish out the sequence of interest from the ocean of unwanted sequence, the depicted approach dries up the ocean, leaving behind the target sequence of interest. Methods may be used to perform such an approach to enrich for long DNA fragments (~50-100 kb) of interest. The fragment may be detected or analyzed, e.g., sequenced by NGS or a long read sequencing platform such as Oxford Nanopore or PacBio. Methods may be used to isolate any length fragment (e.g., 100 bases, 150 bases, 175 bases, etc . . . ) that includes a boundary of an alteration, such as a breakpoint of a fusion event.

In a population of DNA where a clinically informative fusion event is not present, the genomic DNA is digested down to the size of a DNA sequence equivalent to the amount of sequence protected by a single Cas9/gRNA complex. However, in those samples where a clinically informative fusion is present, both binding proteins 301 will be located on the same DNA strand and therefore protecting the segment 226 between the proteins 301 from DNA degradation.

In a preferred embodiment, the binding proteins 301 are provided by Cas endonuclease/guide RNA complexes. Embodiments of the invention use proteins that are originally encoded by genes that are associated with clustered regularly interspaced short palindromic repeats (CRISPR) in bacterial genomes. Preferred embodiments use a CRISPR-associated (Cas) endonuclease. For such embodiments, the binding protein in a Cas endonuclease complexed with a guide RNA that targets the Cas endonuclease to a specific sequence. Any suitable Cas endonuclease or homolog thereof may be used. A Cas endonuclease may be Cas9 (e.g., spCas9), catalytically inactive Cas (dCas such as dCas9), Cpf1, C2c2, others, modified variants thereof, and similar proteins or macromolecular complexes. A first Cas endonuclease/guide RNA complex includes a first Cas endonuclease 303 and a first guide RNA 309. A second Cas endonuclease/guide RNA complex includes a second Cas endonuclease 304 and a second guide RNA 310.

In the preferred embodiments, the two Cas endonuclease complexes (or sets of complexes if nickases are used) define the locus that includes a junction of a known chimeric/fusion chromosome/gene, i.e., the boundary 219. The complexes protect the segment 226 of nucleic acid that includes the boundary 219. One or more exonuclease 331 is used to digest 115 unprotected nucleic acid. In some embodiments, ExoIII and ExoVII destroy all DNA that does not include both binding/protecting sites. The only DNA that remains includes the junction, or boundary 219, of the known chimera (fusion).

As a result of digestion 115 by exonuclease 331, unprotected nucleic acid 227 is removed from the sample. What remains is the segment 226 containing the breakpoint 219, to which the first Cas endonuclease 303 and second Cas endonuclease 304 may remain bound. The method 101 further includes detecting 125 the segment 226 as present after the digestion step. Any suitable detection technique may be used such as, for example, DNA staining; spectrophotometry; sequencing; fluorescent probe hybridization; fluorescence resonance energy transfer; optical microscopy; or electron microscopy.

The Cas9/gRNA complexes may be subsequently or previously labeled using standard procedures, and single molecule analysis identifying coincidence signal of the two Cas9/gRNA complexes located on the same DNA molecule identifies the presence of the clinically informative fusion of interest. The complexes may be fluorescently labeled, e.g., with distinct fluorescent labels such that detecting involves detecting both labels together (e.g., after a dilution into fluid partitions). The complexes may be labeled with a FRET system such that they fluoresce only when bound to the same segment. Preferred embodiments of analysis does not require PCR amplification and therefore significantly reduces cost and sequence bias associated with PCR amplification. Sample analysis can also be performed by a number of approaches such as NGS etc. However, many analytical platforms may require PCR amplification prior to analysis. Therefore, preferred embodiments of analysis of the reaction products include single molecule analysis that avoid the requirement of amplification.

Kits and methods of the invention are useful with methods disclosed in U.S. Provisional Patent Application 62/526,091, filed Jun. 28, 2017, for POLYNUCLEIC ACID MOLECULE ENRICHMENT METHODOLOGIES and U.S. Provisional Patent Application 62/519,051, filed Jun. 13, 2017, for POLYNUCLEIC ACID MOLECULE ENRICHMENT METHODOLOGIES, both incorporated by reference.

Figure 4:
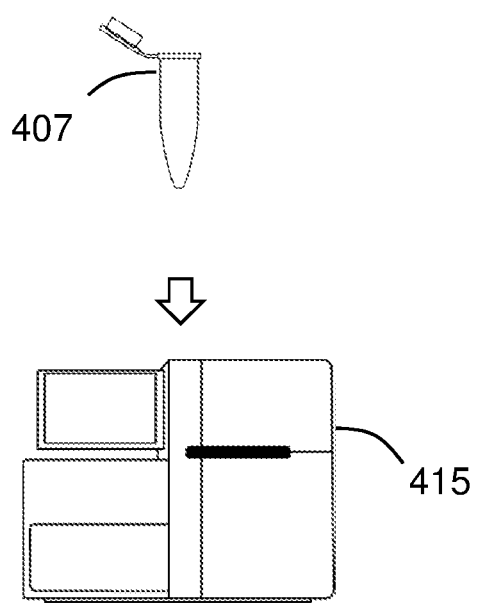
FIG. 4 shows the detection of an isolated segment of nucleic acid.

FIG. 4 shows the detection 125 of the isolated segment 226 of the nucleic acid. The digestion 115 provides a reaction product 407 that includes principally only the segment 226 of nucleic acid, as well as any spent reagents, Cas endonuclease complexes, exonuclease, nucleotide monophosphates, or pyrophosphate as may be present. The reaction product 407 may be provided as an aliquot (e.g., in a micro centrifuge tube such as that sold under the trademark EPPENDORF by Eppendorf North America (Hauppauge, N.Y.) or glass cuvette). The reaction product 407 may be disposed on a substrate. For example, the reaction product may be pipetted onto a glass slide and subsequently combed or dried to extend the fragment 226 across the glass slide. The reaction product may optionally be amplified. Optionally, adaptors are ligated to ends of the reaction product, which adaptors may contain primer sites or sequencing adaptors. The presence of the segment 226 in the reaction product 407 may then be detected using an instrument 415.

The fragment 226 may be detected, sequenced, or counted. Where a plurality of fragment 226 are present or expected, the fragment may be quantified, e.g., by qPCR.

In certain embodiments, the instrument 415 is a spectrophotometer, and the detection 125 includes measuring the adsorption of light by the reaction product 407 to detect the presence of the segment 226. The method 101 may be performed in fluid partitions, such as in droplets on a microfluidic device, such that each detection step is binary (or "digital"). For example, droplets may pass a light source and photodetector on a microfluidic chip and light may be used to detect the presence of a segment of DNA in each droplet (which segment may or may not be amplified as suited to the particular application circumstance). By the described methods, a sample can be assayed for a genomic structural alteration using a technique that is inexpensive, quick, and reliable. Methods of the disclosure are conducive to high throughput embodiments, and may be performed, for example, in droplets on a microfluidic device, to rapidly assay a large number of aliquots from a sample for one or any number of genomic structural alterations.

The Cas endonuclease/guide RNA complexes can be designed to flank suspected gene fusions, or may be designed without a priori knowledge of any such alteration, but introduced to sample nucleic acid in pairs that include guide RNAs with targeting regions complementary to targets that do not appear on the same chromosome in a healthy human genome. The complexes bind to healthy DNA on different chromosomes, so detecting a segment via the described method 101 indicates the presence of a structural alteration in the subject's DNA.

When a genomic structural alteration is thus detected, a report may be provided 135 to, for example, describe the alteration in a patient.

Figure 5:
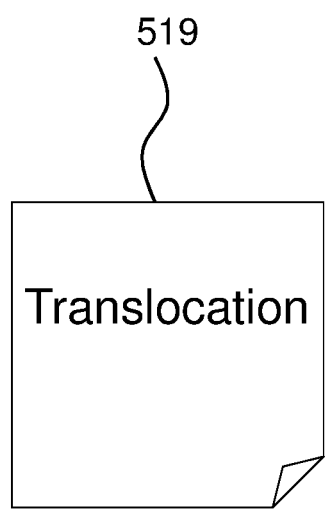
FIG. 5 shows a report describing a structural alteration in nucleic acid from a subject.

FIG. 5 shows a report 519 as may be provided in certain embodiments. The report preferably includes a description of the structural alteration in the subject (e.g., a patient). The method 101 for detecting structural alterations may be used in conjunction with a method of describing mutations (e.g., as described herein). Either or both detection process may be performed over any number of loci in a patient's genome or preferably in a patient's tumor DNA. As such, the report 519 may include a description of a plurality of structural alterations, mutations, or both in the patient's genome or tumor DNA. As such, the report 519 may give a description of a mutational landscape of a tumor.

Knowledge of a mutational landscape of a tumor may be used to inform treatment decisions, monitor therapy, detect remissions, or combinations thereof. For example, where the report 519 includes a description of a plurality of mutations, the report 519 may also include an estimate of a tumor mutation burden (TMB) for a tumor. It may be found that TMB is predictive of success of immunotherapy in treating a tumor, and thus methods described herein may be used for treating a tumor.

Methods of the invention thus may be used to detect and report clinically actionable information about a patient or a tumor in a patient. For example, the method 101 may be used to provide 135 a report describing the presence of the genomic alteration in a genome of a subject. Additionally, protecting 113 a segment 226 of DNA and digesting 115 unprotected DNA provides a method for isolation or enrichment of DNA fragments, i.e., the protected segment. It may be found that the described enrichment technique is well-suited to the isolation/enrichment of arbitrarily long DNA fragments, e.g., thousands to tens of thousands of bases in length.

Long DNA fragment targeted enrichment, or negative enrichment, creates the opportunity of applying long read platforms in clinical diagnostics. Negative enrichment may be used to enrich "representative" genomic regions that can allow an investigator to identify "off rate" when performing CRISPR Cas9 experimentation, as well as enrich for genomic regions that would be used to determine TMB for immuno-oncology associated therapeutic treatments. In such applications, the negative enrichment technology is utilized to enrich large regions (>50 kb) within the genome of interest.

In preferred embodiments, the invention provides methods 101 for detecting structural alterations and/or methods for detecting mutations in DNA.

Figure 6:
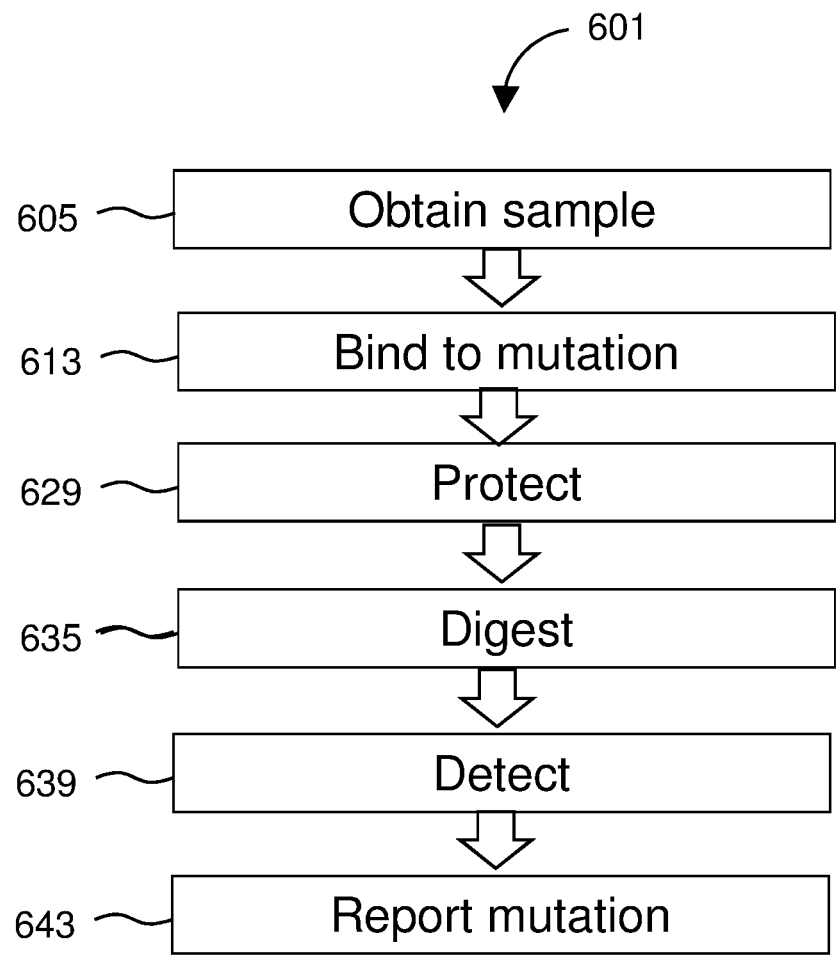
FIG. 6 diagrams a method for detecting a mutation.

FIG. 6 diagrams a method 601 for detecting a mutation. The method 601 includes obtaining 605 a sample that includes DNA from a subject. The sample is exposed to a first Cas endonuclease/guide RNA complex that binds 613 to a mutation in a sequence-specific fashion. The method 601 includes protecting 629 a segment of nucleic acid in a sample by introducing the first Cas endonuclease/guide RNA complex (that binds to a mutation in the nucleic acid) and a second Cas endonuclease/guide RNA complex that also binds to the nucleic acid. Unprotected nucleic acid is digested 635. For example, one or more exonucleases may be introduced that promiscuously digest unbound, unprotected nucleic acid. While the exonucleases act, the segment containing the mutation of interest is protected by the bound complexes and survives the digestion step 635 intact. The method 601 includes detecting 639 the segment, there confirming the presence of the mutation. A report may be provided 643 that describes the mutation as being present in the subject.

The method 601 uses the idea of mutation-specific gene editing, or "allele-specific" gene editing, which may be implemented via complexes that include a Cas endonuclease and an allele-specific guide RNA.

Figure 7:
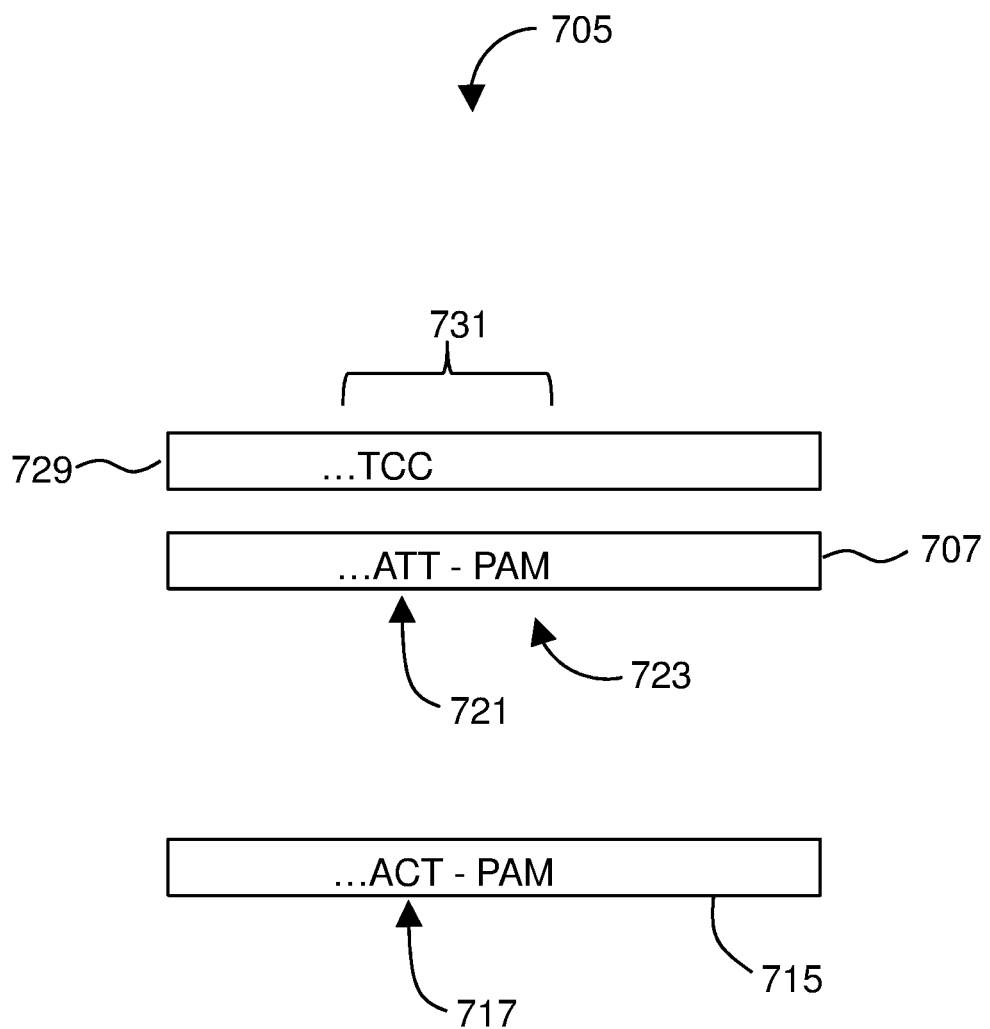
FIG. 7 illustrates an allele-specific guide RNA for mutation detection.

FIG. 7 illustrates the operation of allele-specific guide RNA for mutation detection. A sample 705 may contain a mutant fragment 707 of DNA, a wild-type fragment 715 of DNA, or both. A locus of interest is identified where a mutation 721 may be present proximal to, or within, a protospacer adjacent motif (PAM) 723. When the wild-type fragment 715 is present, it may contain a wild-type allele 717 at a homologous location in the fragment 715, also proximal to, or within, a PAM. A guide RNA 729 is introduced to the sample that has a targeting portion 731 complementary to the portion of the mutant fragment 707 that includes the mutation 721. When a Cas endonuclease is introduced, it will form a complex with the guide RNA 729 and bind to the mutant fragment 707 but not to the wild-type fragment 715. The first Cas endonuclease/guide RNA complex includes a guide RNAs with targeting region that binds to the mutation but that does not bind to other variants at a loci of the mutation.

The described methodology may be used to target a mutation 721 that is proximal to a PAM 723, or it may be used to target and detect a mutation in a PAM, e.g., a loss-of-PAM or gain-of-PAM mutation. The PAM is typically specific to, or defined by, the Cas endonuclease being used. For example, for *Streptococcus* pyogenes Cas9, the PAM include NGG, and the targeted portion includes the 20 bases immediately 5' to the PAM. As such, the targetable portion of the DNA includes any twenty-three consecutive bases that terminate in GG or that are mutated to terminate in GG. Such a pattern may be found to be distributed over a genome at such frequency that the potentially detectable mutations are abundant enough as to be representative of mutations over the genome at large. In such cases, allele-specific negative enrichment may be used to detect mutations in targetable portions of a genome. Moreover, the method 601 may be used to determine a number of mutations over the representative, targetable portion of the genome. Since the targetable portion of the genome is representative of the genome overall, the number of mutations may be used to infer a mutational burden for the genome overall. Where the sample includes tumor DNA and the mutations are detected in tumor DNA, the method 601 may be used to give a tumor mutation burden.

The method 601 includes the described negative enrichment, in which a segment of nucleic acid in a sample is protected 629 by a first Cas endonuclease/guide RNA complex (that binds to a mutation in the nucleic acid) and a second Cas endonuclease/guide RNA complex that also binds to the nucleic acid.

Figure 8:
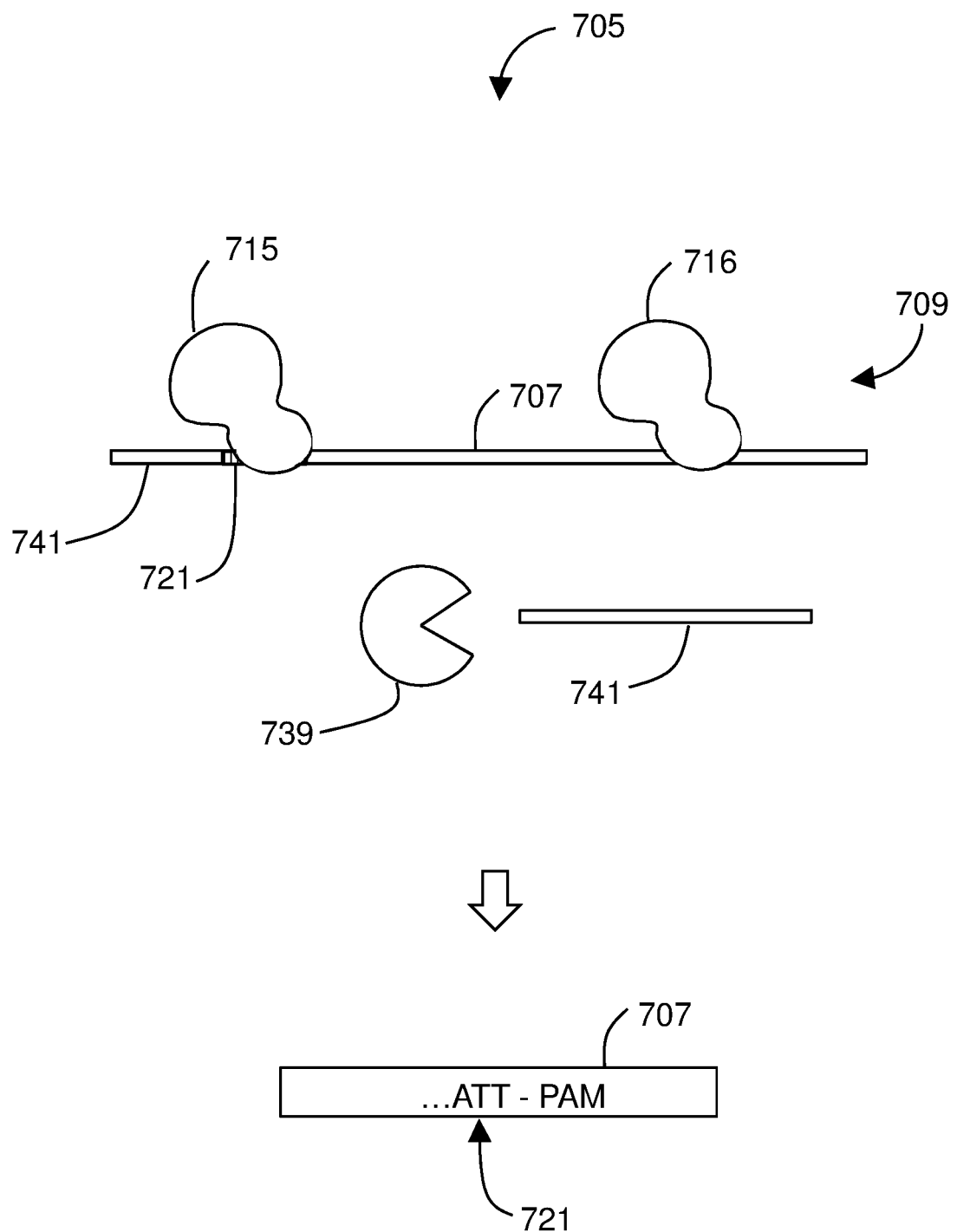
FIG. 8 illustrates a negative enrichment.

FIG. 8 illustrates operation of the negative enrichment. The sample 705 includes DNA 709 from a subject. The sample 705 is exposed to a first Cas endonuclease/guide RNA complex 715 that binds to a mutant fragment 707 mutation in a sequence-specific fashion. Specifically, the complex 715 binds to the mutation 721 in a sequence-specific manner. A segment of the nucleic acid 709, i.e., the mutant fragment 707, is protected by introducing the first Cas endonuclease/guide RNA complex 715 (that binds to a mutation in the nucleic acid) and a second Cas endonuclease/guide RNA complex 716 that also binds to the nucleic acid. Unprotected nucleic acid 741 is digested. For example, one or more exonucleases 739 may be introduced that promiscuously digest unbound, unprotected nucleic acid 741. While the exonucleases 739 act, the segment containing the mutation of interest, the mutant fragment 707, is protected by the bound complexes 715, 716 and survives the digestion step intact.

The described steps including the digestion by the exonuclease 739 leaves a reaction product that includes principally only the mutant segment 707 of nucleic acid, as well as any spent reagents, Cas endonuclease complexes, exonuclease 739, nucleotide monophosphates, and pyrophosphate as may be present. The method 601 includes detecting 639 the segment 707 (which includes the mutation 721). Any suitable technique may be used to detect 639 the segment 707. For example, detection may be performed using DNA staining, spectrophotometry, sequencing, fluorescent probe hybridization, fluorescence resonance energy transfer, optical microscopy, electron microscopy, others, or combinations thereof. Detecting the mutant segment 707 indicates the presence of the mutation in the subject (i.e., a patient), and the a report may be provided describing the mutation in the patient.

A feature of the method 601 is that a specific mutation may be detected by a technique that includes detecting only the presence or absence of a fragment of DNA, and it need not be necessary to sequence DNA from a subject to describe mutations. The method 601, the method 101, or both may be performed in fluid partitions, such as in droplets on a microfluidic device, such that each detection step is binary (or "digital"). For example, droplets may pass a light source and photodetector on a microfluidic chip and light may be used to detect the presence of a segment of DNA in each droplet (which segment may or may not be amplified as suited to the particular application circumstance).

The method 601 uses a double-protection to select one or both ends of DNA segments. The gRNA selects for a known mutation on one end. If it doesn't find the mutation, no protection is provided and the molecule gets digested. The remaining molecules are either counted or sequenced. The method 601 is well suited for the analysis of small portions of DNA, degraded samples, samples in which the target of interest is extremely rare, and particularly for the analysis of maternal serum (e.g., for fetal DNA) or a liquid biopsy (e.g., for ctDNA).

The method 601 and the method 101 include a negative enrichment step that leaves the target loci of interest intact and isolated as a segment of DNA. The methods are useful for the isolation of intact DNA fragments of any arbitrary length and may preferably be used in some embodiments to isolate (or enrich for) arbitrarily long fragments of DNA, e.g., tens, hundreds, thousands, or tens of thousands of bases in length or longer. Long, isolated, intact fragments of DNA may be analyzed by any suitable method such as simple detection (e.g., via staining with ethidium bromide) or by single-molecule sequencing. Embodiments of the invention provide kits that may be used in performing methods described herein.

Figure 9:
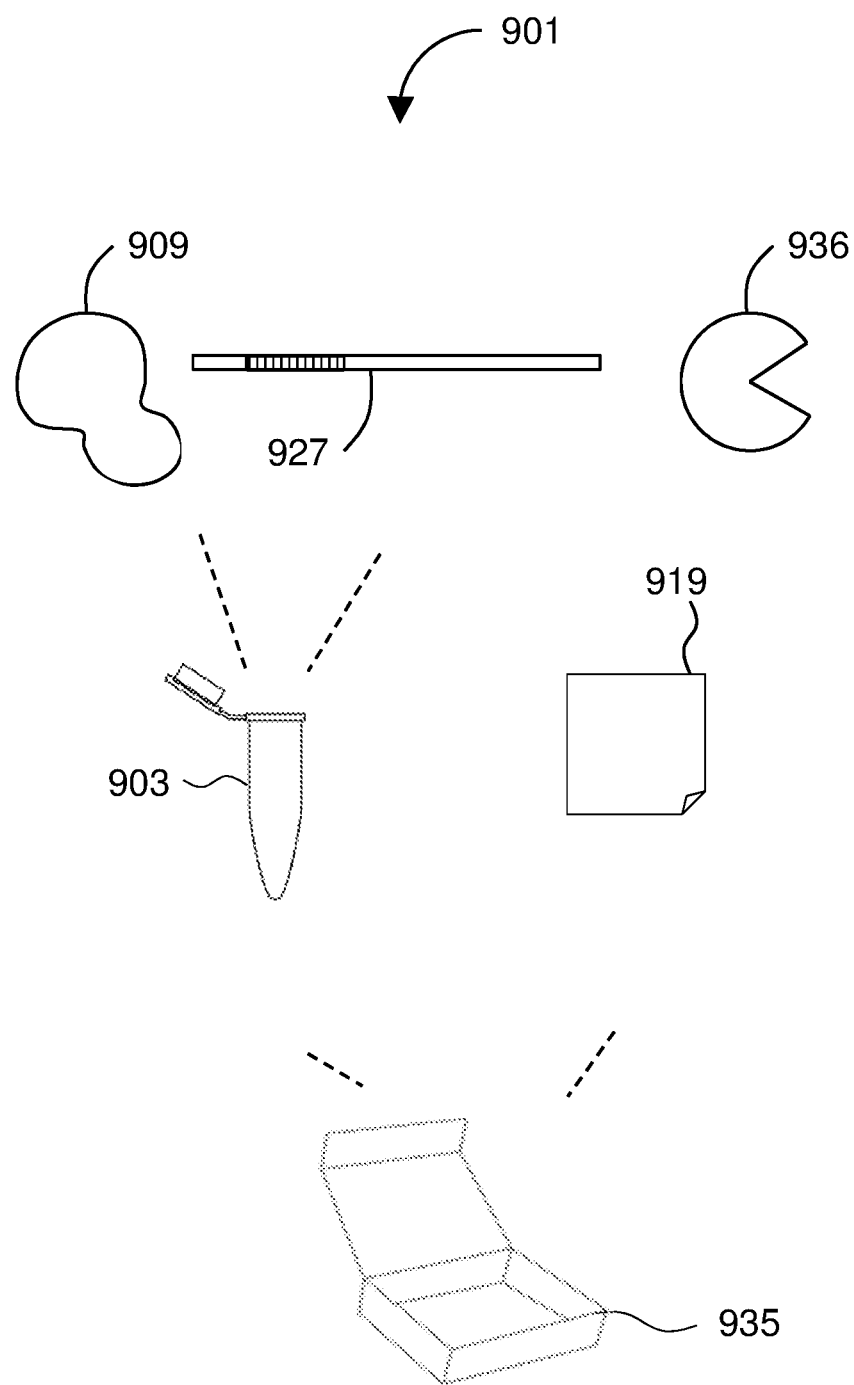
FIG. 9 shows a kit of the invention.

FIG. 9 shows a kit 901 of the invention. The kit 901 may include reagents 903 for performing the steps described herein. For example, the reagents 903 may include one or more of a Cas endonuclease 909, a guide RNA 927, and exonuclease 936. The kit 901 may also include instructions 919 or other materials such as pre-formatted report shells that receive information from the methods to provide a report (e.g., by uploading from a computer in a clinical services lab to a server to be accessed by a geneticist in a clinic to use in patient counseling). The reagents 903, instructions 919, and any other useful materials may be packaged in a suitable container 935. Kits of the invention may be made to order. For example, an investigator may use, e.g., an online tool to design guide RNA and reagents for the performance of methods 101, 601. The guide RNAs 927 may be synthesized using a suitable synthesis instrument. The synthesis instrument may be used to synthesize oligonucleotides such as gRNAs or single-guide RNAs (sgRNAs). Any suitable instrument or chemistry may be used to synthesize a gRNA. In some embodiments, the synthesis instrument is the MerMade 4 DNA/RNA synthesizer from Bioautomation (Irving, Tex.). Such an instrument can synthesize up to 12 different oligonucleotides simultaneously using either 50, 200, or 1,000 nanomole prepacked columns. The synthesis instrument can prepare a large number of guide RNAs 927 per run. These molecules (e.g., oligos) can be made using individual prepacked columns (e.g., arrayed in groups of 96) or well-plates. The resultant reagents 903 (e.g., guide RNAs 917, endonuclease(s) 909, exonucleases 936) can be packaged in a container 935 for shipping as a kit.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for detecting a genomic structural alteration, the method comprising:
protecting a segment of nucleic acid in a sample by introducing Cas endonuclease/guide RNA complexes that bind to targets that flank a breakpoint of a genomic structural alteration selected from the group consisting of inversion, translocation, copy number variation, and gene duplication;
digesting unprotected nucleic acid, wherein the digesting comprises exposing the unprotected nucleic acid to one or more exonucleases; and
detecting the segment, thereby confirming the presence of the genomic alteration.

2. The method of claim 1, wherein the Cas endonuclease/guide RNA complexes include guide RNAs with targeting regions complementary to targets that do not appear on the same chromosome in a healthy human genome.

3. The method of claim 1, wherein one or more of the Cas endonuclease/guide RNA complexes includes a reporter.

4. The method of claim 3, wherein the reporter includes a fluorescent reporter linked to a Cas endonuclease.

5. The method of claim 1, wherein the detecting step includes one selected from the group consisting of DNA staining; spectrophotometry; sequencing; fluorescent probe hybridization; fluorescence resonance energy transfer; optical microscopy; and electron microscopy.

6. The method of claim 1, further comprising isolating the segment as an intact fragment of DNA with a length of at least five thousand bases.

7. The method of claim 1, further comprising providing a report describing the presence of the genomic structural alteration in a genome of a subject.

8. The method of claim 1, wherein the sample includes plasma from the subject and the segment is cell-free DNA (cfDNA).

9. The method of claim 8, wherein the plasma is maternal plasma and the segment is of fetal DNA.

10. The method of claim 1, wherein the sample comprises a liquid biopsy.

11. The method of claim 1, wherein the sample includes plasma from the subject and the segment is circulating tumor DNA (ctDNA).

12. The method of claim 1, wherein the sample includes at least one circulating tumor cell from a tumor and the segment comprises tumor DNA from the tumor cell.

13. A method for detecting a mutation, the method comprising:
protecting a segment of a nucleic acid in a sample by introducing a first Cas endonuclease/guide RNA complex that binds to a mutation in the nucleic acid and a second Cas endonuclease/guide RNA complex that binds to the nucleic acid at a location that does not include the mutation;
digesting unprotected nucleic acid, wherein the digesting comprises exposing the unprotected nucleic acid to one or more exonucleases while the first Cas endonuclease/guide RNA complex and the second Cas endonuclease/guide RNA complex protect the segment from digestion; and
detecting the segment, thereby confirming the presence of the mutation.

14. The method of claim 13, wherein the first Cas endonuclease/guide RNA complex includes a guide RNA with targeting region that binds to the mutation but that does not bind to other variants at a loci of the mutation.

15. The method of claim 13, wherein the detecting step includes one selected from the group consisting of DNA staining; spectrophotometry; sequencing; fluorescent probe hybridization; fluorescence resonance energy transfer; optical microscopy; and electron microscopy.

16. The method of claim 13, wherein one or more of the Cas endonuclease/guide RNA complexes includes a reporter.

17. The method of claim 13, further comprising isolating the segment as an intact fragment of DNA with a length of at least five thousand bases.

18. The method of claim 13, further comprising providing a report describing the presence of the mutation in a genome of a subject.

19. The method of claim 13, wherein the sample includes plasma from the subject and the segment is cell-free DNA (cfDNA).

20. The method of claim 19, wherein the plasma is maternal plasma and the segment is of fetal DNA.

21. The method of claim 13, wherein the sample includes plasma from the subject and the segment is circulating tumor DNA (ctDNA).

22. The method of claim 13, wherein the sample comprises a liquid biopsy.

23. The method of claim 13, wherein the sample includes at least one circulating tumor cell from a tumor and the segment comprises tumor DNA from the tumor cell.

* * * * *